United States Patent
Abedin et al.

(10) Patent No.: US 10,434,240 B2
(45) Date of Patent: Oct. 8, 2019

(54) METHODS AND SYSTEMS FOR PROCESSING AND WASHING A PHOTOPHERESIS MONONUCLEAR CELL PRODUCT

(71) Applicant: Fenwal, Inc., Lake Zurich, IL (US)

(72) Inventors: Tanima Jahan Abedin, Chicago, IL (US); Katherine N. Radwanski, Des Plaines, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 14/828,226

(22) Filed: Aug. 17, 2015

(65) Prior Publication Data

US 2017/0049951 A1    Feb. 23, 2017

(51) Int. Cl.
| | |
|---|---|
| *A61M 1/02* | (2006.01) |
| *A61M 1/34* | (2006.01) |
| *A61M 1/36* | (2006.01) |
| *A61M 1/38* | (2006.01) |
| *A61K 35/14* | (2015.01) |
| *A61K 41/00* | (2006.01) |

(52) U.S. Cl.
CPC ........... *A61M 1/3693* (2013.01); *A61K 35/14* (2013.01); *A61K 41/0057* (2013.01); *A61M 1/3496* (2013.01); *A61M 1/3683* (2014.02); *A61M 1/3686* (2014.02); *A61M 1/3696* (2014.02); *A61M 1/38* (2013.01); *A61M 1/0209* (2013.01); *A61M 2202/0407* (2013.01); *A61M 2202/0439* (2013.01); *A61M 2205/12* (2013.01); *A61M 2205/128* (2013.01)

(58) Field of Classification Search
None
See application file for complete search history.

(56) References Cited

U.S. PATENT DOCUMENTS

| | | |
|---|---|---|
| 4,568,328 A | 2/1986 | King |
| 4,578,056 A | 3/1986 | King et al. |
| 4,683,889 A | 8/1987 | Edelson |
| 4,838,852 A | 6/1989 | Edelson et al. |
| 5,104,373 A | 8/1992 | Davidner et al. |
| 5,316,667 A | 5/1994 | Brown et al. |
| 5,360,542 A | 11/1994 | Williamson, IV et al. |
| 5,383,847 A | 1/1995 | Edelson |
| 5,951,509 A | 9/1999 | Morris |
| 5,984,887 A | 11/1999 | McLaughlin et al. |
| 6,027,657 A | 2/2000 | Min et al. |
| 6,219,584 B1 | 4/2001 | Lee |
| 6,245,570 B1 | 6/2001 | Grimm |
| 6,582,386 B2 | 6/2003 | Min et al. |
| 6,793,643 B1 | 9/2004 | Briggs |
| 6,986,867 B2 | 1/2006 | Hanley et al. |
| 7,025,877 B1 | 4/2006 | de Gheldere et al. |
| 7,476,209 B2 | 1/2009 | Gara et al. |
| 7,601,298 B2 | 10/2009 | Waldo et al. |
| 7,727,523 B2 | 6/2010 | Edelson et al. |
| 7,846,121 B2 | 12/2010 | Wuepper |
| 7,850,634 B2 | 12/2010 | Briggs |
| 8,057,418 B2 | 11/2011 | Korbling et al. |
| 8,556,844 B2 | 10/2013 | Leonard |
| 2010/0210989 A1 | 8/2010 | Macpherson et al. |
| 2013/0197419 A1 | 8/2013 | Min et al. |
| 2013/0252227 A1 | 9/2013 | Min et al. |
| 2014/0370491 A1 | 12/2014 | Radwanski |
| 2015/0196706 A1 | 7/2015 | Radwanski et al. |
| 2015/0359959 A1 | 12/2015 | Radwanski et al. |
| 2016/0114095 A1 | 4/2016 | Radwanski |

FOREIGN PATENT DOCUMENTS

| | | |
|---|---|---|
| EP | 1 066 842 A2 | 1/2001 |
| EP | 0 951 305 B1 | 10/2004 |
| EP | 2 520 165 A1 | 11/2012 |
| EP | 2 620 171 A1 | 7/2013 |
| WO | WO 96/22117 | 7/1996 |
| WO | WO 2012/125457 A1 | 9/2012 |

OTHER PUBLICATIONS

Extended European Search Report dated Dec. 14, 2016 for Application No. 16183386.8.

*Primary Examiner* — Allison M Fox
(74) *Attorney, Agent, or Firm* — Cook Alex Ltd.

(57) ABSTRACT

Methods and systems for the treatment and post-treatment processing of a mononuclear cell product are disclosed. The methods and systems include and provide for the separation of excess conditioning fluid and unbound treating agent prior to return of said treated mononuclear cell product to a patient.

13 Claims, 9 Drawing Sheets

METHODS AND SYSTEMS FOR PROCESSING AND WASHING A PHOTOPHERESIS MONONUCLEAR CELL PRODUCT

FIELD OF THE DISCLOSURE

The present disclosure is directed to methods and systems for the processing and washing of a photopheresis-treated mononuclear cell product. More particularly, the present disclosure is directed to methods and systems of washing a treated mononuclear cell product to remove excess photoactivation agent and excess solution prior to return of the treated product to the subject.

BACKGROUND

Light irradiation therapy is used for the treatment of various blood diseases to, e.g., eliminate immunogenicity in cells, inactivate or kill selected cells, inactivate viruses or bacteria, or activate desirable immune responses. For example, it is known to use the photoactivatable compound 8-methoxypsoralen (8-MOP) to treat blood cells, such as lymphocytes, in an extracorporeal photopheresis (ECP) procedure. In one example of such a procedure, blood is withdrawn from the patient and the white blood cells, which are mononuclear cells, are separated (typically by centrifugation) from the remainder of the whole blood components. The separated white blood cells are combined with a selected dose of 8-MOP and subjected to light (typically UV-A) to activate the 8-MOP molecules. The light crosslinks 8-MOP to DNA strands inside the cell and on the cell wall of the exposed leukocytes, eventually causing cell apoptosis. The fluid with the altered white blood cells is reinfused back into the patient to induce an immune system response. Examples of a photopheresis method and system of the type described above are set forth in U.S. Patent Application Publication Nos. US2013/0197419 and US2014/0370491, the contents of both incorporated herein by reference in their entireties.

In order to administer an effective amount of activating light (e.g., UV-A) to the mononuclear cells, the mononuclear cell product must have a hematocrit and thickness that allows for the administered light to be effective in the treatment of the mononuclear cells. For example, if the hematocrit is too high—indicating too many red cells—the residual red blood cells may interfere with the light treatment, i.e., activation of the photoactivation agent, resulting in a less than fully treated mononuclear cell product. A conditioning solution, such as saline, may be used to increase the volume of and dilute the fluid in which the collected mononuclear cells reside to ensure that the correct thickness and hematocrit is reached in the container of cells to be treated. The photoactivation agent is likewise added to the mononuclear cells (e.g., in an irradiation container) and this mixture is irradiated in an illumination device with light. The treated cells are then returned to the patient.

The reinfusion of the treated cells may, however, also cause some undesired side effects in the patient. For example, the presence of unbound photoactivation agent in the patient's circulatory system may create certain discomforting conditions for the patient, such as light sensitivity and an increased susceptibility to sun burn. In addition to the potential side effects of unbound photoactivation agent, the amount of the conditioning solution used may be excessive and result in hypervolemia, which can be problematic for patients with cardiovascular problems. In mononuclear cell procedures in general, the amount of anticoagulant and saline returned to the patient is often much greater than the collected MNC volume, thereby causing a fluid imbalance in the patient. Therefore, it would be desirable to remove the excess conditioning solution and photoactivation agent from the treated cells, divert them and prevent them from being returned to the patient during an extracorporeal photopheresis procedure. The methods and systems described herein address this need.

SUMMARY

In one aspect, the present disclosure is directed to a method for treating a cellular product in a cell therapy. The method includes collecting, in a unitary disposable fluid circuit, a desired cellular product from a source of a biological fluid that includes the desired cells. The collected cellular product is then combined with (1) a conditioning solution in an amount effective to arrive at a desired hematocrit for the collected cell product and (2) a treating agent in an amount effective for the cell treatment within the fluid circuit. The method includes treating the cellular product to arrive at a treated product. The treated product is introduced into a separation chamber mounted on a separator device where it is separated within the fluid circuit into a treated mononuclear cell fraction and a supernatant fraction. The treated mononuclear cell fraction is directed through the fluid circuit to a patient, while the supernatant fraction is diverted elsewhere.

In another aspect, the present disclosure is directed to a system for treating a cellular product in a cell therapy including a first reusable hardware unit that includes a separator, one or more pumps, one or more valves, an interface detecting unit and a controller programmed for selectively operating the one or more pumps based on information obtained from the interface detecting unit. The system also includes a second reusable hardware unit that includes at least one light source and a chamber positioned in a field of light emitted by the at least one light source, the chamber being configured to receive a container of cellular product.

The system further includes a disposable fluid circuit that is mountable on the reusable hardware unit. The disposable fluid circuit includes a venous access member for accessing the circulatory system of the subject, a container for receiving a fraction of a treated cell product and at least one chamber associated with the separator for separating a treated mononuclear cell fraction from a supernatant fraction. The disposable fluid circuit further includes ports associated with the at least one chamber for directing the treated mononuclear cell fraction to the access member and a port for diverting the supernatant fraction elsewhere.

DETAILED DESCRIPTION OF THE EMBODIMENTS

The present disclosure is directed to methods and systems for the collection, treatment and reinfusion of mononuclear cells. The methods and systems of the present disclosure are described in connection with particular apheresis and irradiation/illumination devices for purposes of exemplification only. It will be understood that the methods and systems described and claimed herein may be carried out and provided in combination with other apheresis and/or irradiation/illumination devices that will be known to those of skill in the art.

Figure 1:
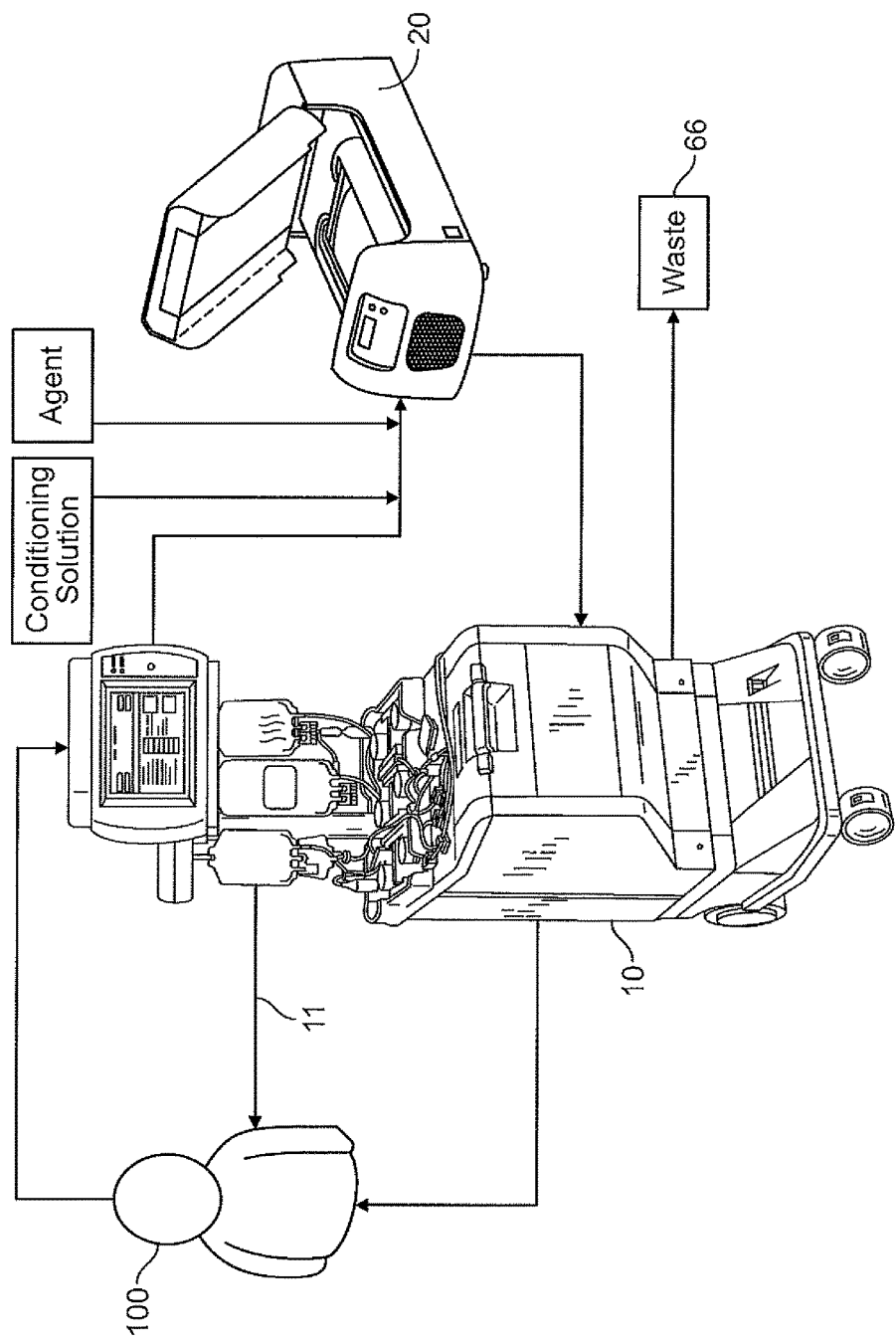
FIG. 1 is a diagram of the system and method for processing a mononuclear cell product in accordance with the present disclosure.

Turning now to the Figures, FIG. 1 diagrammatically shows the system and processing steps in the method described herein. In accordance with the present disclosure, the system includes a separation component or separator 10 and a treatment or irradiation component 20. In one embodiment, irradiation component 20 is independent and housed separately from separator 10. Although separately housed and independent devices, it is preferable that separator 10 and irradiation device 20 be located adjacent to each other. While FIG. 1 shows a preferred embodiment of the individual separation and irradiation components, it will be appreciated that the methods described herein may also be used with devices having integrated separation and irradiation components housed in one device.

As shown in FIG. 1, whole blood is withdrawn from the patient 100 and introduced into the separator 10 where the whole blood is separated to provide a target cell population. More particularly, whole blood is withdrawn from the patient through venipuncture needle 82 (FIG. 2) and introduced into the separation chamber of separation container 12 carried within and/or mounted on a centrifuge device of separator 10. Within the separator 10, the target cell population is separated from other components. In a preferred embodiment in accordance with the present disclosure, the target cell population is the patient's mononuclear cells (MNC). Other components separated from the whole blood in this initial separation, such as red blood cells and platelets, may be returned to the patient or collected in pre-attached containers of the blood processing set, as shown by line 11.

The separated target cell population, e.g., mononuclear cells with residual red blood cells and plasma, is then prepared for treatment and irradiation in treatment component 20. In accordance with the present disclosure, effective treatment of the mononuclear cells with ultraviolet light requires that the collected mononuclear cells be provided in a suspension having a reduced amount of light attenuating material, such as red blood cells. Specifically, the amount of red blood cells in the MNC suspension to be treated affects the amount of UV light that the MNC are exposed to as the red blood cells in the MNC suspension will block at least a portion the UV light from reaching the targeted MNCs.

Accordingly, in order to prepare or otherwise condition the collected mononuclear cells for the photoactivation treatment, the collected cell product may be combined (diluted) with a conditioning solution to adjust the hematocrit of the collected cell product and arrive at a selected thickness of the cell product in the treatment container to allow for effective and at least substantially complete treatment of the product within the treatment chamber of treatment apparatus 20. The collected cell product is also combined with an effective amount of the photoactivation agent. As shown in FIG. 1, addition of the conditioning solution and the photoactivation agent may occur after collection of the desired cellular product in separator 10. As described below, the conditioning solution may be added from a container 64 (shown in FIG. 2) directly to the container that holds the collected MNC product. The photoactivation agent may likewise be added from a container or by a syringe or other delivery device. Alternatively, the conditioning solution and/or photoactivation agent may be introduced elsewhere in the processing circuit 200 of FIG. 2 for combination with the collected cell product (in, for example, container 68). In one embodiment, the conditioning solution may be saline and the photoactive agent may be 8-methoxypsoralen (8-MOP).

In accordance with the present disclosure, after treatment in device 20, the now-treated mononuclear cells are subjected to further processing in separator 10 prior to return to the patient. Inasmuch as the treated cell products will typically include excess conditioning solution and unbound photoactivation agent, it may be desirable to remove the same by "washing" the treated cell product. If washing of the treated mononuclear cells is performed, the suspension of mononuclear cells is preferably subjected to a centrifugal field (or other separation principle which can effect separation of the fluid components) in a separation chamber of separator 10, whereby the mononuclear cells are concentrated into a treated mononuclear cell fraction and separated from the supernatant fraction which includes any remaining unbound photoactivation agent and excess conditioning solution. The supernatant fraction may then be diverted to an appropriate waste container 66, while the treated mononuclear cell fraction is returned to the patient, as generally shown in FIG. 1.

Turning now, more specifically, to one embodiment of the reusable hardware and disposable fluid circuit components of the system, device/separator 10 useful in the collection (and washing) of mononuclear cells include the Amicus® Separator made and sold by Fresenius-Kabi USA, of Lake Zurich, Ill. Mononuclear cell collections using a device such as the Amicus® are described in greater detail in U.S. Pat. No. 6,027,657, the contents of which is incorporated by reference herein in its entirety. Briefly, FIGS. 3-4 show a representative blood centrifuge device/separator 10 with fluid circuit 200 mounted thereon, the fluid circuit 200 having a blood processing container 14 (see FIG. 2) defining a separation chamber suitable for harvesting mononuclear cells from whole blood. As shown in FIG. 3, a portion of disposable processing set or fluid circuit 200 is mounted on the front panel of device/separator 10. As also shown in FIG. 4, separation chamber 12, which is integral with the rest of circuit 200, is defined by the walls of a flexible processing container 14 carried within an annular gap defined by a rotating spool element 18 and an outer bowl element (not shown) housed within the cabinet of device/separator 10.

The processing container 14 takes the form of an elongated tube or belt which is wrapped about the spool element 18 before use. The bowl and spool element 18 are pivoted on a yoke between an upright position and a suspended position, also not shown. In operation, the centrifuge device within separator 10 rotates the suspended bowl and spool element 18 about an axis, creating a centrifugal field within the processing chamber of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

Figure 2:
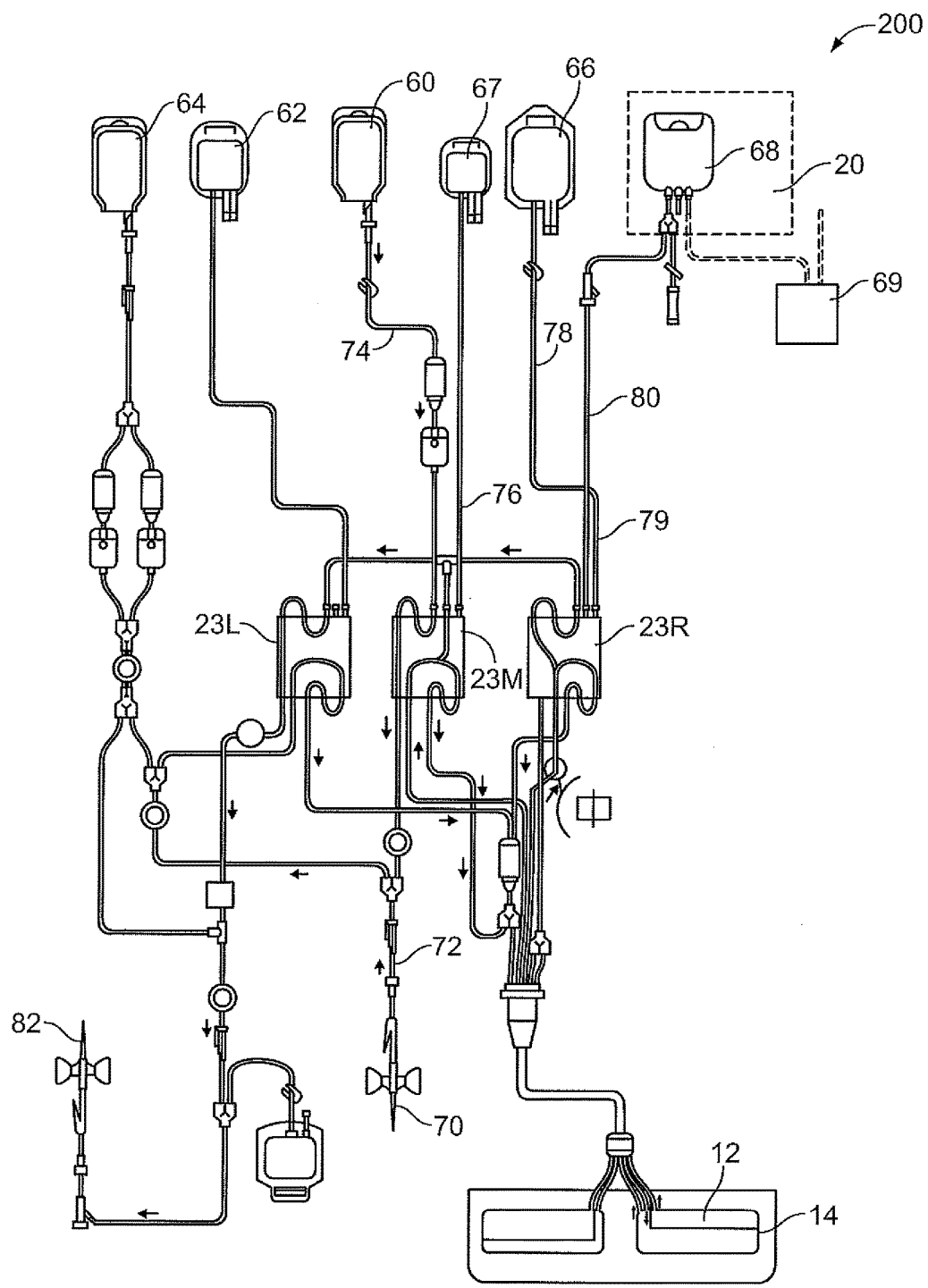
FIG. 2 is a diagram of a disposable fluid circuit suitable for use with the system of the present disclosure.
Figure 3:
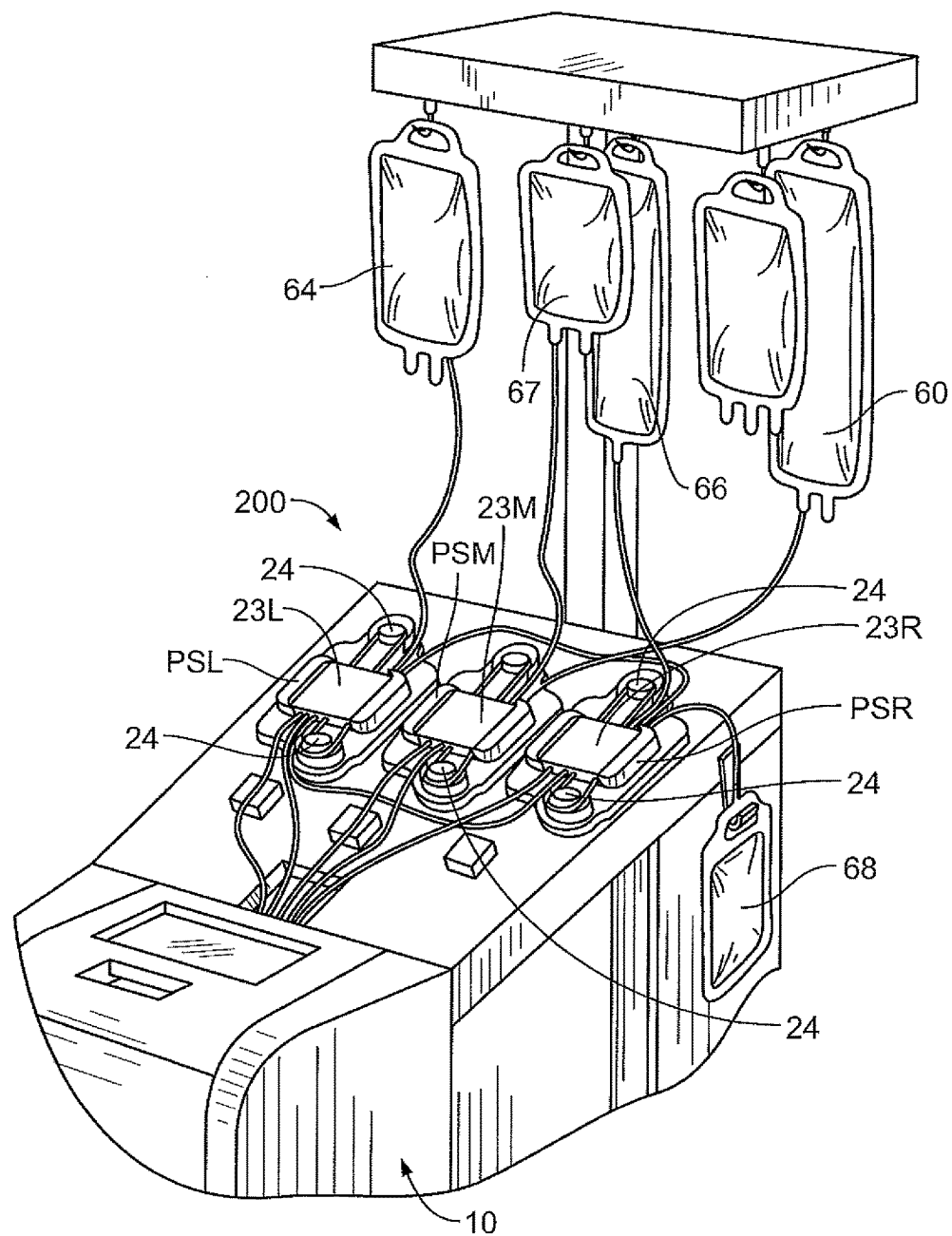
FIG. 3 is a partial perspective view of the front panel of a multifunctional apheresis separator useful in the methods and systems described herein with the disposable fluid circuit mounted thereon.
Figure 4:
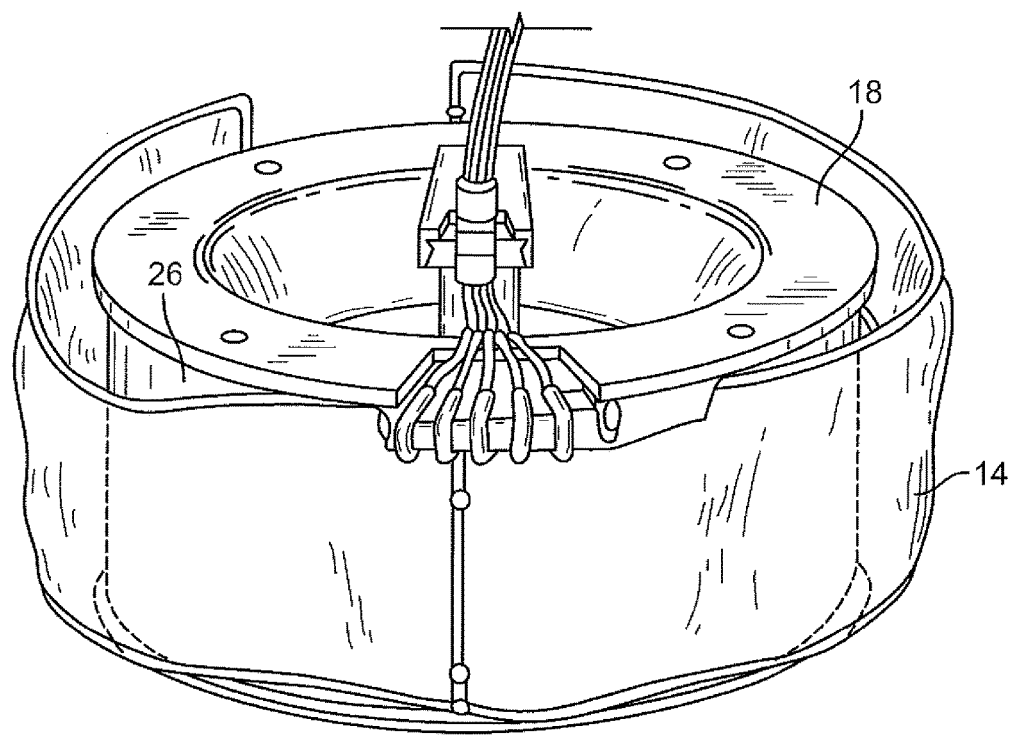
FIG. 4 is a perspective view of a processing container (separation chamber) of the fluid circuit used with the separator.

With reference to FIGS. 2-3, fluid circuit 200 includes a plurality of processing fluid flow cassettes 23L, 23M and 23R with tubing loops for association with peristaltic pumps 24 on device 10. As described in U.S. Pat. No. 6,027,657, previously incorporated by reference, cassettes 23L, 23M and 23R include molded plastic bodies with integrally molded liquid flow channels. Valve stations (depicted as numbered circles within each cassette and best seen in FIGS. 7-9) are molded into the backside of cassette bodies. A flexible diaphragm covers and seals the backside of the cassette (23) body. Valve stations align with valve actuators of pump stations (PSL, PSM and PSR) located on the front panel of device 10. Fluid circuit 200 also includes a network of tubing and pre-connected containers for establishing flow communication with the patient and for processing and collecting fluids and blood and blood components, as shown in greater detail in FIG. 2.

As seen in FIGS. 2 and 3, in one embodiment disposable processing set 200 may include a container 60 for supplying anticoagulant, a waste container 62 for collecting waste from one or more steps in the process for collecting, treating and/or washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and is preferably pre-attached to the disposable set 200. Alternatively, container 68 may be attached to set 200 by known sterile connection techniques, such as sterile docking or the like. With reference to FIG. 2, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more venipuncture needle(s) for accessing the circulatory system of the patient. As shown in FIG. 2, fluid circuit 200 includes inlet needle 70 and return needle 82. In an alternative embodiment, a single needle can serve as both the inlet and outlet needle.

Container 68 is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Accordingly, as indicated above, container 68 in which the mononuclear cells are collected may serve both as the collection container and the irradiation container. Container 68 may be placed inside irradiation device 20 by the operator or, more preferably, may be placed inside the irradiation chamber of irradiation device 20 at the beginning of the ECP procedure and prior to whole blood withdrawal (as shown by the broken lines representing device 20 in FIG. 2). In any event, container 68 preferably remains integrally connected to the remainder of fluid circuit 200 during the entire procedure, thereby maintaining the closed or functionally closed condition of fluid circuit 200.

Fluid flow through fluid circuit 200 is preferably driven, controlled and adjusted by a microprocessor-based controller in cooperation with the valves, pumps, weight scales and sensors of device 10, the details of which are described in the previously mentioned U.S. Pat. No. 6,027,657. As described below, the controller is programmed to activate rotation of pumps (and control the rotational speed thereof), associated with cassettes 23L, 23M and 23R, open and close valves, receive output signals from sensors and detectors, such as the interface detection system described below, and the like. The fluid circuit is further adapted for association with the treatment component (i.e., irradiation device) 20.

In accordance with the systems and methods described herein a patient is connected to a blood processing set, i.e., fluid circuit 200. As generally illustrated in FIGS. 2 and 3, fluid circuit 200 provides a sterile closed pathway between separation component 10 and irradiation component 20. The system described herein also preferably includes a washing component, which may be housed within the separation component. Preferably, the separation component 10 and washing component are one and the same. In one embodiment, the separation component and/or washing component 10 may be the centrifuge-based separator (such as, but not limited to the Amicus®) described above.

Alternatively, the washing component may operate in accordance with a different separation principle. For example, washing component 10 may include a separate device such as a spinning porous membrane of the type described in International Patent Application Publication No. WO 2012/125457, incorporated herein by reference. The spinning membrane separator may be used for separating the treated mononuclear cell fraction from the supernatant fraction. It will be understood that a reusable hardware component utilizing a separation principle other than centrifugation, such as the aforementioned spinning membrane may also include a microprocessor-based controller that controls the pumps, valves and sensors. In addition, the reusable hardware component utilizing a spinning membrane principle of separation will be configured to receive at least a portion of the disposable fluid circuit or a disposable fluid circuit of the type disclosed in WO2012/125457.

The separation between the treated cell fraction and supernatant fraction may be sensed or monitored to ensure efficient separation. Accordingly, in one embodiment, where separation is achieved by centrifugation, the system may include an interface detecting unit that monitors the location of the interface. The interface detection unit may be of the type described in U.S. Pat. No. 6,027,657, previously incorporated by reference. The interface detection unit may be the same interface detection unit used during the initial separation of whole blood into two or more components. After the initial separation has been completed and separation chamber 12 is used to separate the treated mononuclear cell fraction from the supernatant fraction, an interface detection unit monitors the location of the interface between these fractions.

Figure 6A:
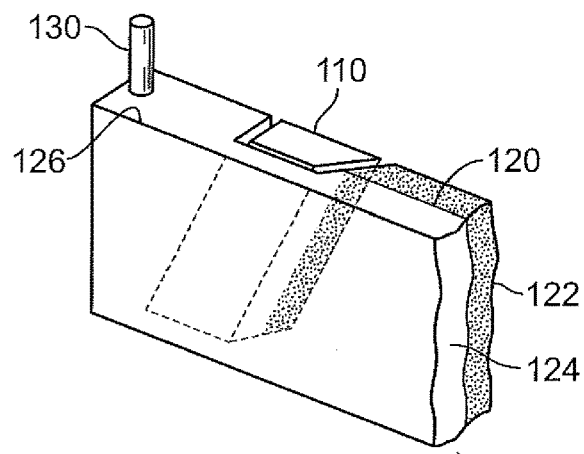
FIGS. 6 (*a*)-(*c*) is a series of enlarged perspective views of an interface ramp carried by the centrifuge and the interface between the treated mononuclear cell fraction and supernatant fraction in different locations (a)-(c)
Figure 6B:
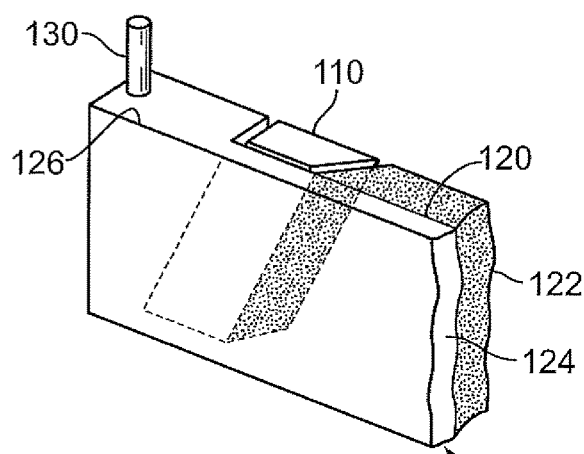
Figure 6C:
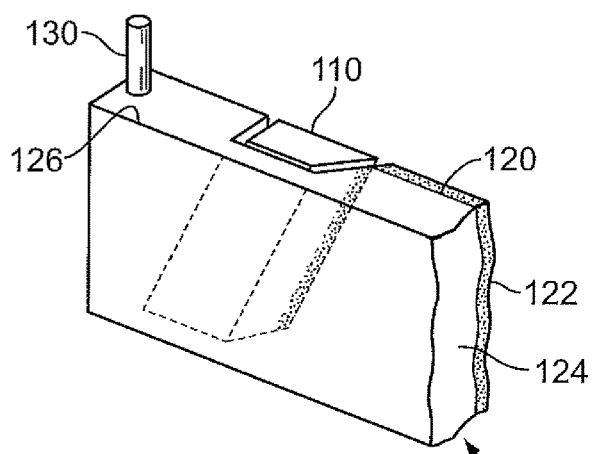

As described in U.S. Pat. No. 6,027,657, a ramp 110 may be provided in combination with a light source and a light detector to determine the radial position of the interface between the treated mononuclear cell fraction and the supernatant fraction. FIGS. 6(a)-6(c) show an exemplary ramp which extends from the inner surface of the bowl (not shown) toward spool 18 (FIGS. 6(a)-6(c)).

As shown in FIGS. 6(a)-6(c), during the step of separating the treated mononuclear cell fraction from the supernatant fraction, an interface 120 is formed between the fractions in separation chamber 12. The heavier treated mononuclear cell fraction 122 accumulates along the "high G" wall, while the supernatant fraction 124 occupies the area of chamber 12 nearer the "low G" wall 126. An exit port 130 communicates with chamber 12 and allows for removal of supernatant fraction from chamber 12 and diversion of supernatant fraction 124 to waste container 66. In accordance with the present disclosure, interface 120 is optimally positioned such that substantially all of the supernatant fraction can exit chamber 12 through port 130 to the substantial exclusion of the treated mononuclear cell fraction 122. If interface 120 is positioned too close to the "high G" wall, as shown in FIG. 6(c), some of the supernatant which includes some of the photoactivation agent and excess conditioning fluid will undesirably be sent back to the patient. On the other hand, if interface 120 approaches the "low G" wall 126, as shown in FIG. 6(b), some of the treated mononuclear cell fraction 124 will undesirably be diverted to waste container 66.

Thus, if the interface detector unit senses the position of interface 120 outside of its optimal position, as shown in FIG. 6(a), for example, it will send a signal output to the controller, as also described in U.S. Pat. No. 5,316,667, incorporated herein by reference. The controller, in turn, will adjust the speed of the peristaltic pump associated with cassette that acts on the line leading to the waste container to accelerate or slow the rotation of such pump and thereby adjust the interface to its more optimal position. In one embodiment, the speed of pump rotation of the pump responsible for introducing fluid into separation chamber 12 (for example, pump 24L) associated with cassette 23L may be fixed. The speed of pump 24R which may be associated with the flow path for removing supernatant from separation chamber 12 may be varied by the controller depending on the location of the interface between the treated mononuclear cell fraction from the supernatant fraction.

As for a system that utilizes a different principle of separation for the step of separating the treated fraction from the supernatant fraction, such as but not limited to, the spinning membrane system previously described, an interface detection and control system may not be required and a different type of sensing or sensing unit may be employed for ensuring efficient separation of the treated mononuclear cell fraction from the supernatant fraction.

Figure 5:
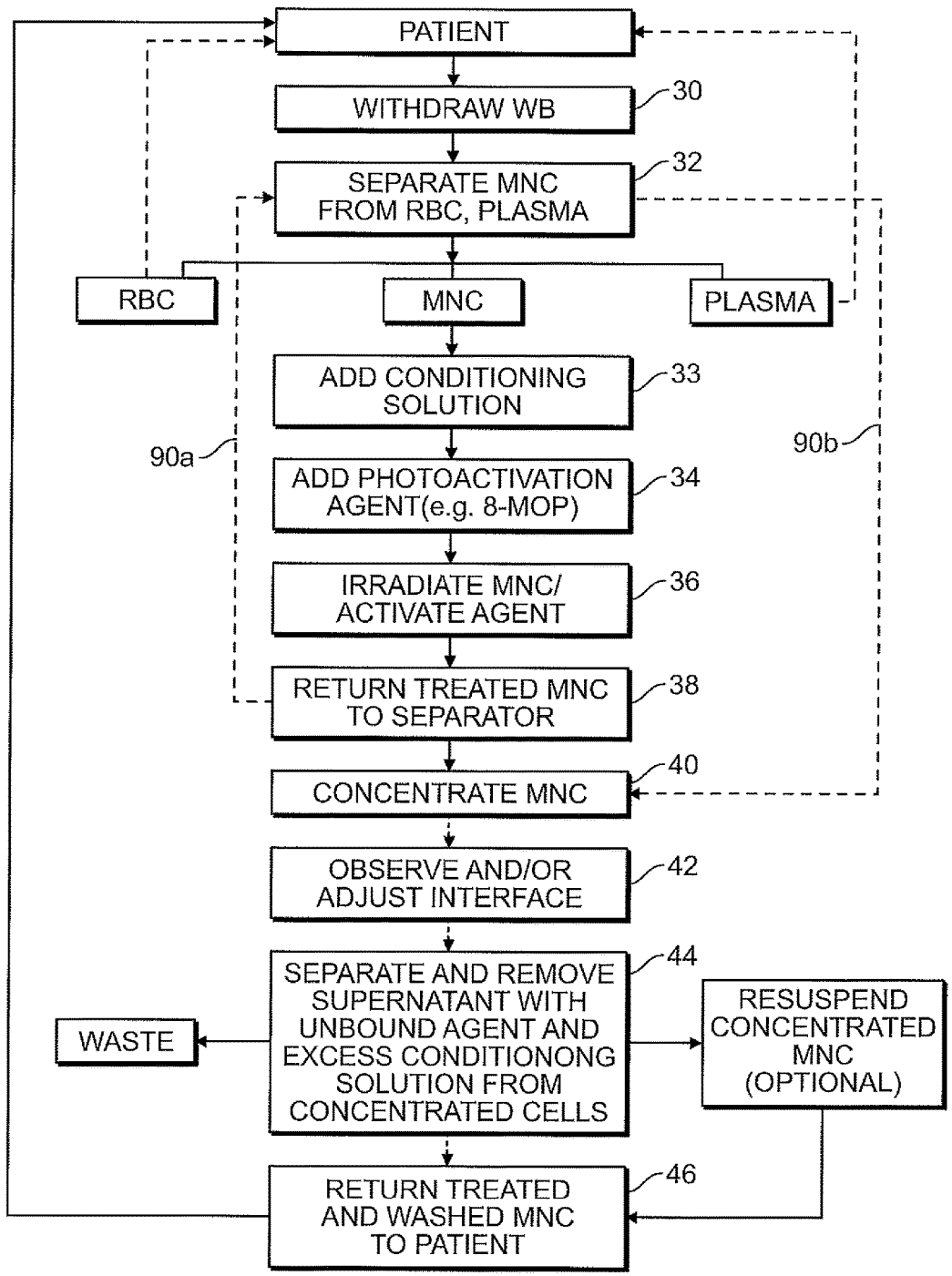
FIG. 5 is a flow chart indicating steps of the method of the present disclosure.

Turning now to the method of treating mononuclear cells, as shown in FIG. 5, whole blood is withdrawn from a patient (step 30) through inlet needle 70 and introduced into the separation chamber 12 of container 14 of processing set 200, where the whole blood is subjected to a centrifugal field provided by separator 10. The centrifugal field will separate the target cell population, i.e., mononuclear cells, from red blood cells, platelets and plasma (step 32). As discussed above, the components such as red blood cells and platelets may be returned to the patient or may be diverted to a container (e.g., container 67) for further processing.

Collection of the mononuclear cells may proceed in one or more cycles. The number of processing cycles conducted in a given therapeutic procedure will depend upon the total volume of WB to be processed. For example, in a representative procedure, five collection cycles may be performed sequentially. During each cycle about 1500-3000 ml of whole blood can be processed to obtain a MNC volume of about 3-5 ml per cycle, resulting in a total volume of 15-25 ml of MNCs. The final volume of mononuclear cells is collected in collection container 68 (FIG. 2) from which it is then provided for further treatment in accordance with the present disclosure. Of course, the collection of MNC is not limited to the method described above. MNCs may be collected in any manner known to those of skill in the art.

Effective treatment of the mononuclear cells with light may require that the amount of collected mononuclear cells have a suitable hematocrit. Thus, it may be desired or even necessary to dilute the mononuclear cells with a conditioning fluid, such as saline, as shown in step 33. In the example described above, approximately 15 ml of MNC may be diluted in about 200 ml of saline.

The diluted mononuclear cells (in container 68) are then combined with the suitable photoactivation agent in step 34. Alternatively, the desired volume of the agent may be pre-added to the container. As discussed above, for ECP treatment, the compound 8-methoxypsoralen (8-MOP) has been shown to be an effective photoactivation agent. However, other suitable photoactivation agents may be used, including, for example, other psoralen compounds. In one example, the system, under the direction of the microprocessor-based controller, may be programmed to automatically deliver the desired amount of photoactive agent from, for example, container 69 before or after the MNC collection, based on the volume of MNC collected or to be collected. For example, 8-MOP may be pre-added to container 68 at the beginning of a particular procedure or alternatively, added to the MNCs collected in the container just prior to irradiation. The 8-MOP is combined with the collected and diluted mononuclear cells to arrive at a mixture having, for example, a final 8-MOP concentration of 100-400 nanograms/mL. In one embodiment, the mononuclear cells may be combined with the photoactivation agent to arrive at a final 8-MOP concentration in a range of about 200 nanograms/mL. As an alternative to introduction from container 69, the 8-MOP or other photoactivation agent may be added directly to container 68 by a syringe through a port in the container, or added elsewhere in fluid circuit 200 also by a syringe.

The mononuclear cells with photoactivation agent (8-MOP) are then irradiated for a selected period of time (step 36). In one non-limiting example, during treatment, the mononuclear cell product may be exposed to UV bulbs having a wavelength in the UVA range of about 320 nm to 400 nm for a selected period of time, such as approximately 10-60 minutes, resulting in an average UVA exposure of approximately 0.5-5.0 $J/cm^2$ and use preferably approximately 1-2 $J/cm^2$ or even more preferably approximately 1.5 $J/cm^2$ per MNC.

Once treatment is complete, the treated mononuclear cells may be returned to separator 10 (and more specifically, the separation chamber 12 of container 14) as shown in step 38 of FIG. 5. For example, one of the pumps associated with cassette 23R may be actuated (automatically by the controller or under the manual control of the operator) to withdraw the treated MNC from container 68 and introduce the MNC into chamber 12 of container 14. Once inside chamber 12, the MNC may be concentrated (step 40). Supernatant, which will include unbound photoactivation agent is separated from the concentrated and treated cells and diverted to a waste container.

The treated MNC are separated from remaining supernatant (step 44) under the influence of centrifugal field, in the case where a centrifugal separator is used (or by the spinning action of a spinning membrane). During separation, the interface between the treated mononuclear cell fraction and supernatant fraction is periodically or continuously observed or monitored for proper positioning (step 42). If necessary, the interface is adjusted. Any remaining unbound and excess photoactive agent and excess conditioning solution will be separated from the concentrated mononuclear cells and suspended in the supernatant. The supernatant may then be withdrawn to a waste container 62 (FIG. 4) while the concentrated and washed mononuclear cells may optionally be resuspended with a resuspension solution (such as, but not limited to, plasma or saline) as shown in step 45, and returned back to the patient, as shown in step 46 of FIG. 5. Other residual blood components remaining in the fluid circuit may also be used to flush or push out the concentrated and washed MNCs and return them to the patient.

In an alternative embodiment, instead of re-introducing only the treated mononuclear cells (with supernatant) into the separator, the treated mononuclear cells may be introduced back into the separator 10 together with whole blood from the patient (typically as an additional cycle after cell treatment) such that the combined streams are subjected to separation under the influence of the centrifugal field to undergo a combined collection/separation cycle. During such additional cycle, the mononuclear cells concentrate in the (separation chamber 12) of separator 10 while platelet-rich plasma separated from the incoming whole blood and the supernatant fraction from the treated mononuclear cells are sent to a waste container and concentrated red blood cells are sent back to the patient. After all of the treated cells from the additional cycle have been reintroduced into the chamber, the mononuclear cells are returned to the patient by, for example, flushing or pushing out the cells with saline or other blood components. This additional cycle is shown in FIG. 5 by dashed lines 90a and 90b where the treated cell product is combined with incoming whole blood at step 32. Once the MNC from both the whole blood and the treated cell product have been combined, no further addition of conditioning solution or treating agent or any further treatment are required. In this additional cycle, the MNC are concentrated as in step 40 and further processed as set forth in steps 42-46.

Figure 7:
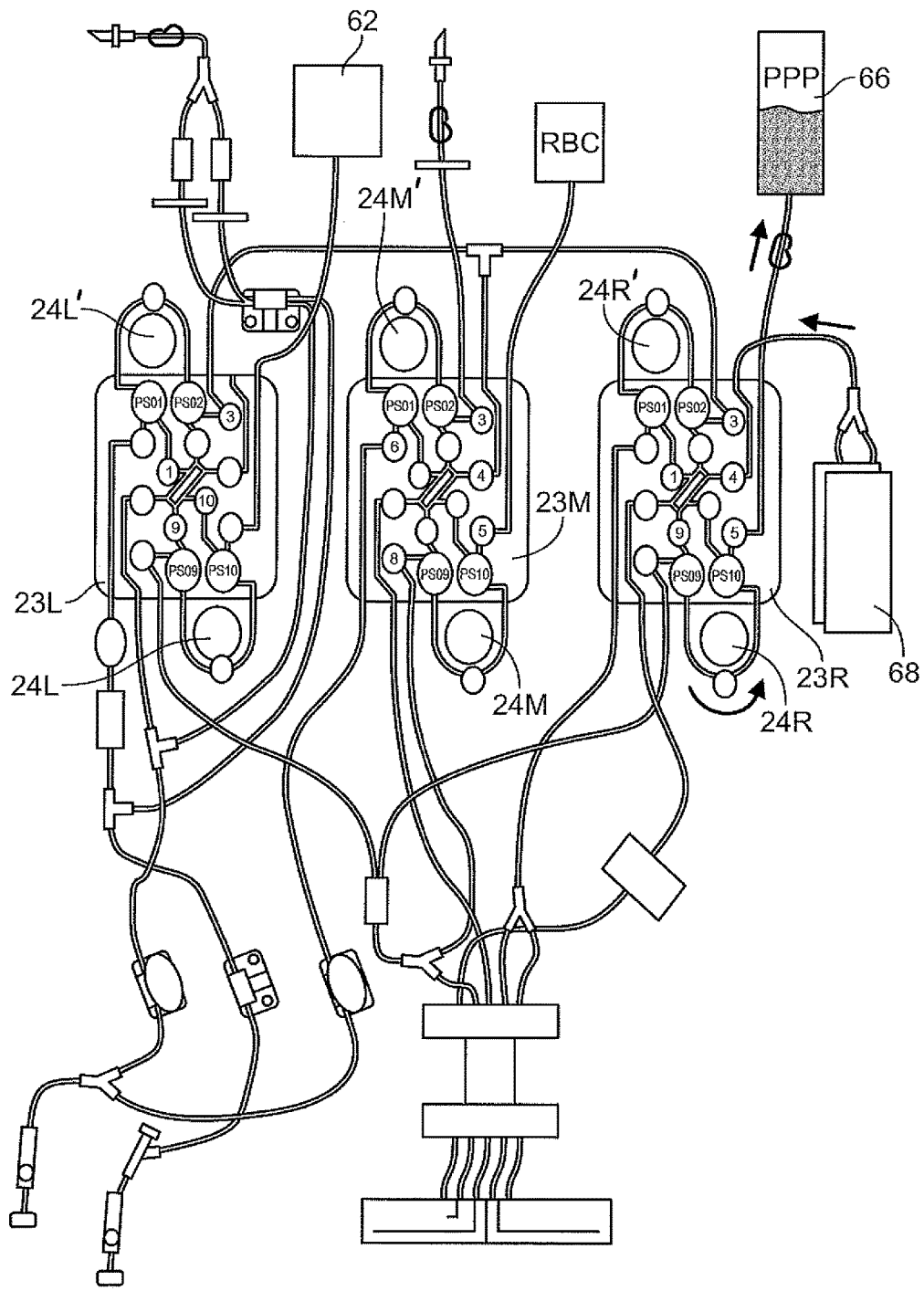
FIG. 7 is a diagram of the disposable fluid processing circuit and the flow of fluid therethrough during one phase of the method of the present disclosure.
Figure 8:
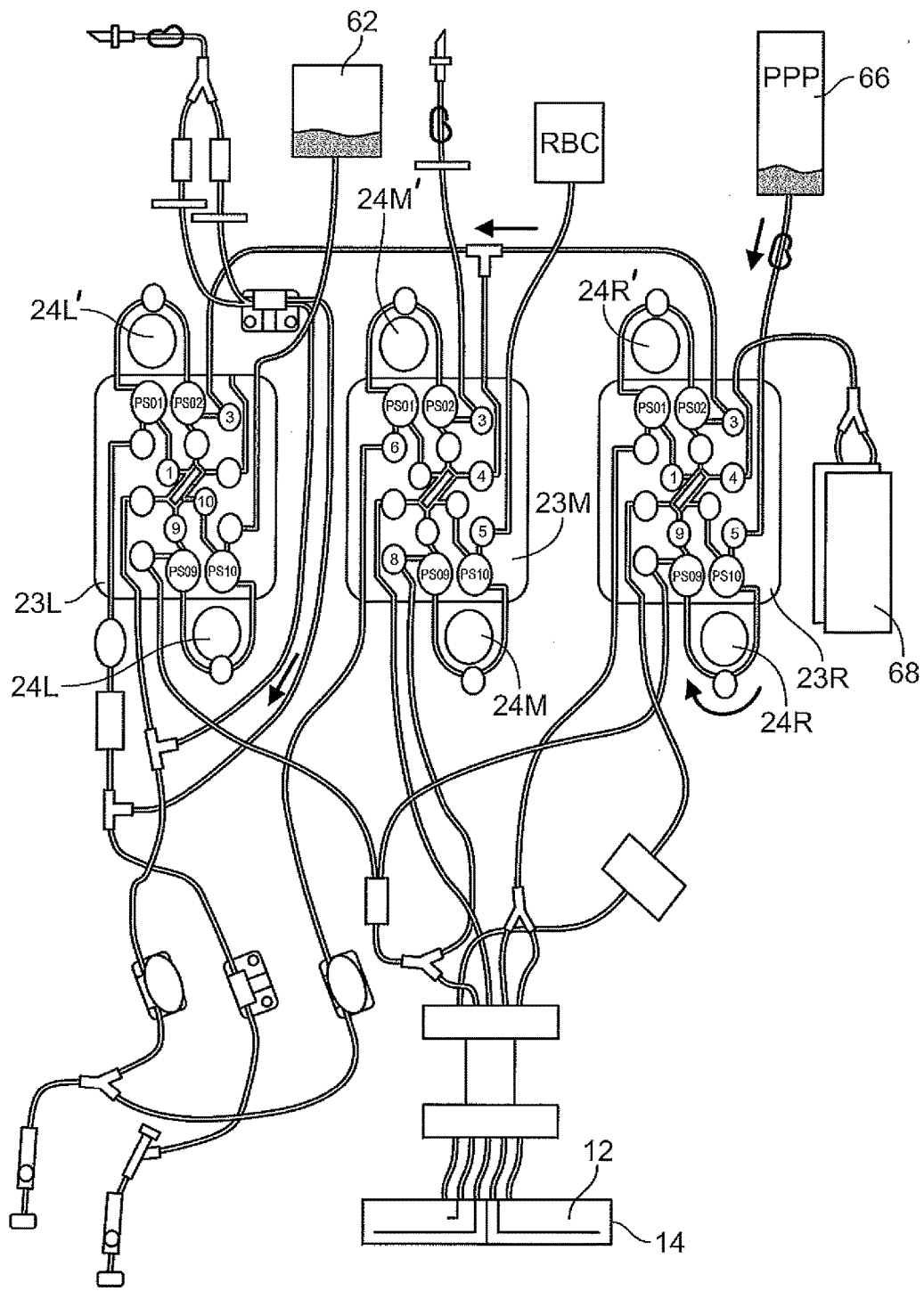
FIG. 8 is a diagram of the disposable fluid processing circuit and the flow of fluid therethrough during another phase of the method of the present disclosure.
Figure 9:
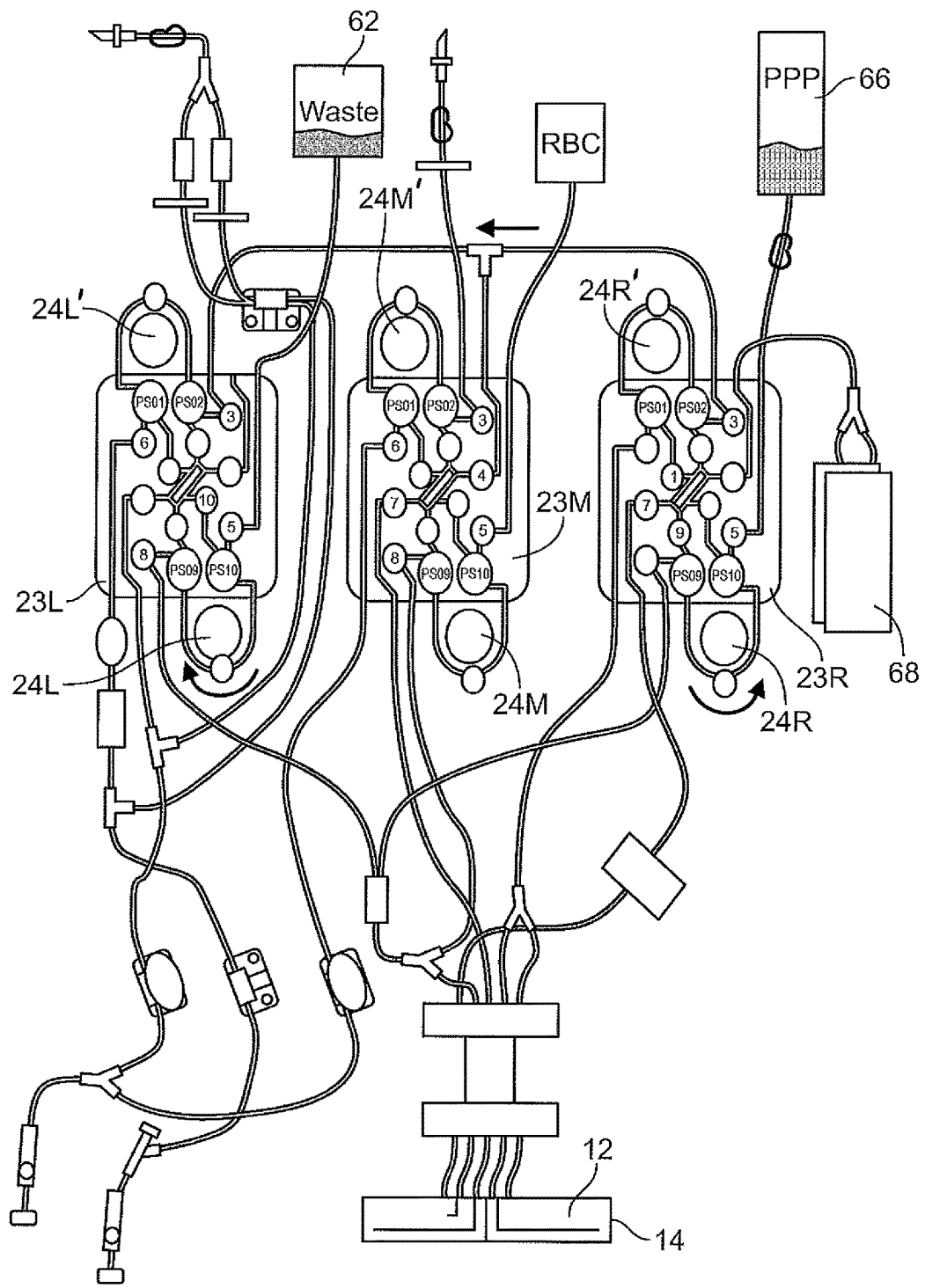
FIG. 9 is a diagram of the disposable fluid processing circuit and the flow of fluid therethrough during still a further phase of the method of the present disclosure.

FIGS. 7-9 show a particular sequence of steps where the method of the present disclosure is carried out using the specific fluid circuit 200 including three (3) cassettes 23L, 23M and 23R. It will be understood that the particular sequence and use of particular pumps, valves and containers are not intended to limit the invention in any way or suggest that different sequences could not be employed. Thus, the description that follows is provided for exemplary purposes only.

As shown in FIG. 7, treated MNC (in container 68) may be transferred to emptied container 66 (initially the PPP container) by action of pump 24R. By selectively opening and closing valves of cassette 23R, the treated MNC may be delivered to chamber 12 of container 14. Alternatively, the treated MNC may be transferred to another container, such as (waste) container 62 from which the treated MNC product is pumped by pump 24L to chamber 12 of container 14 for separation of the treated mononuclear cell fraction from the supernatant fraction, as shown in FIG. 8. As the treated MNC product is introduced into chamber 12, the separated, treated MNC fraction is removed from chamber 12 through middle cassette 23M and returned to the patient (together with other residual blood components still residing in circuit 200), while the supernatant fraction is pumped out via action of pump 24 R to container 66 (FIG. 9). As discussed above, pump 24R is operated by the controller based on output signals received from the interface detection unit.

Other Aspects

In addition to the aspects set forth in the above summary, description, and the claims that follow, there are other aspects of the present subject matter which may be embodied separately or together in the methods and systems described and claimed below. These aspects may be employed alone or in combination with the other aspects of the subject matter described herein, and the description of these aspects together is not intended to preclude the use of these aspects separately or the claiming of such aspects separately or in different combinations, as set forth in the claims appended hereto.

In a first aspect, a method for treating a cellular product in a cell therapy is provided. The method includes collecting a desired cellular product from a source of a biological fluid including desired cells in a unitary disposable fluid circuit. The method also includes combining the cellular product with a conditioning solution in an amount effective to arrive at a desired dilution of a collected cell product and for treatment within the fluid circuit. The cellular product is combined with a treating agent in an amount effective for the cell treatment within the fluid circuit. The cellular product is then treated to arrive at a treated product. The treated product is introduced into a separation chamber of a separator where the treated product is separated to arrive at a treated cell fraction and a supernatant fraction. The treated cell fraction is directed to the patient.

In accordance with a second aspect of the present subject matter, which may be used with the first aspect, the treated product may be separated by centrifugation.

In accordance with a third aspect of the present subject matter, which may be used with the method of the second aspect, the method may include processing the treated product in a separation chamber by centrifugation and establishing an interface during the centrifugation between the treated cell fraction and the supernatant fraction.

In accordance with a fourth aspect of the present subject matter, which may be used with the method of the third aspect, the method may include detecting the location of the interface within the chamber.

In accordance with a fifth aspect of the present subject matter, which may be used with the method of the fourth aspect, the method may include commencing directing the treated cell fraction to the patient upon detection of the interface at a selected location.

In accordance with a sixth aspect of the present subject matter, which may be used with the method of any one of the first through fifth aspects, the method may include diverting the supernatant fraction to a waste container.

In accordance with a seventh aspect of the present subject matter, which may be used with the methods of any one of the first through sixth aspects, the conditioning solution may be saline.

In accordance with an eighth aspect of the present subject matter, which may be used with the methods of any one of the first through seventh aspects, the method may include combining the treated product with the biological fluid and separating mononuclear cells from the combined treated product and the biological fluid.

In accordance with a ninth aspect of the present subject matter, which may be used with the method of the sixth aspect, the method may include diverting the supernatant fraction by pumping the fraction from the chamber to a waste container.

In accordance with a tenth aspect of the present subject matter, which may be used with the method of the ninth aspect, the method may include pumping the supernatant fraction by a peristaltic pump at a selected pump speed.

In accordance with an eleventh aspect of the present subject matter, which may be used with any one of the methods of the first through tenth aspects, the method may include collecting the treated product in a collection container.

In accordance with a twelfth aspect of the present subject matter, which may be used with the method of the eleventh aspect, the method may include transferring the treated product from the chamber of the separator to a collection container.

In accordance with a thirteenth aspect of the present subject matter, which may be used with the method of the twelfth aspect, the method may include reintroducing the treated product into the separator.

In accordance with a fourteenth aspect of the present subject matter, which may be used with the method of the thirteenth aspect, the method may include transferring the treated product from the collection container to a source container prior to reintroducing the treated product into the separator.

In accordance with a fifteenth aspect of the present subject matter, a system for treating a cellular product in a cell therapy is provided. The system includes a first reusable hardware unit, a separator, one or more pumps and one or more valves, and a sensing unit. The system further includes a controller for selectively operating the one or more valves, based on information obtained from the sensing unit. The system also includes a second reusable hardware unit that includes at least one light source and a chamber positioned in a field of light emitted by the at least one light source. The chamber is configured to receive a container of cellular product. The system also includes a disposable fluid circuit mounted on at least the first reusable hardware unit, the circuit including a subject access member, a container for receiving a fraction of a treated cell product, and at least one chamber for separating a treated separated mononuclear cell fraction from a supernatant fraction associated with a separator. Ports associated with at least one chamber for diverting the mononuclear cell fraction to the subject access member and for diverting the supernatant fraction to a container are also provided.

In a sixteenth aspect of the present subject matter, which may be used with the system of the fifteenth aspect, the sensing unit includes an interface detecting unit associated with the separation chamber.

In a seventeenth aspect of the present subject matter, which may be used with the system of the sixteenth aspect, the controller is programmed to divert the treated mononuclear fraction to the subject when the interface detecting unit detects a predetermined position of an interface between the treated mononuclear fraction and the treated supernatant fraction.

In an eighteenth aspect of the present subject matter, which may be used with any one of the fifteenth through seventeenth aspects, the system includes a pump for delivering a treated mononuclear cell fraction through the fluid circuit to the at least one chamber and a pump for withdrawing the supernatant fraction through the fluid circuit from the chamber.

In a nineteenth aspect of the present subject matter, which may be used with any one of the fifteenth through eighteenth aspects, the disposable fluid circuit includes at least one cassette including valving regions and at least one cassette configured for interaction with a pumping element, wherein the cassette is mountable on the reusable hardware unit.

In accordance with a twentieth aspect of the present subject matter, which may be used with any one of the fifteenth through nineteenth aspects, the disposable fluid circuit includes a portion associated with a first reusable hardware unit and a portion associated with a second reusable hardware unit.

In a twenty-first aspect of the present subject matter, which may be used with the system of the twentieth aspect, the disposable fluid processing circuit is a functionally closed system.

In accordance with a twenty-second aspect of the present subject matter, which may be used with the system of the twentieth aspect, the disposable fluid circuit may be a closed system.

In a twenty-third aspect of the present subject matter, which may be used with the system of the fifteenth aspect, the separator is a centrifugal separator.

In accordance with a twenty-fourth aspect of the present subject matter, which may be used with the system of the fifteenth aspect, the system may include a spinning membrane separator.

It will be understood that the embodiments and examples described above are illustrative of some of the applications or the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method for treating a cellular product in a cell therapy comprising:
  a) collecting a desired cellular product from a source of a biological fluid including desired cells in a unitary disposable fluid circuit mounted on a reusable hardware unit comprising a separator, valves, pumps, weight scales and sensors;
  b) combining said cellular product with a conditioning solution in an amount effective to arrive at a desired dilution of the collected cell product for said treatment within said fluid circuit;
  c) combining said cellular product with a treating agent in an amount effective for said cell treatment within said fluid circuit;
  d) treating said cellular product to arrive at a treated product in a treatment container;
  e) combining said treated product of step (d) with whole blood to arrive at a combined treated product and whole blood;
  f) introducing said combined treated product and whole blood into a separator chamber of said separator;
  g) separating a supernatant fraction from said combined treated product and whole blood within said separator to arrive at a combined cellular fraction and a supernatant fraction;
  h) establishing an optimal interface between said combined cellular fraction and said supernatant fraction;

i) positioning said interface such that substantially all of said supernatant fraction exits said separator chamber to the substantial exclusion of said combined cellular fraction; and j) substantially maintaining said position by fixing flow of said combined treated product and whole blood into said separation chamber and/or adjusting flow of said supernatant fraction exiting the separation chamber.

2. The method of claim 1 comprising separating said combined treated product and whole blood in step (g) by centrifugation.

3. The method of claim 1 comprising monitoring the location of the interface between said supernatant fraction and said combined cellular fraction within said chamber.

4. The method of claim 3 comprising commencing directing said combined cellular fraction to said patient upon detection of the interface at a selected location.

5. The method of claim 4 further comprising flushing said disposable fluid circuit with blood components residing in said fluid circuit and returning said blood components to said patient with said combined cellular fraction treated.

6. The method of claim 1 wherein said conditioning solution comprises saline.

7. The method of claim 1 comprising diverting said supernatant fraction by pumping said supernatant fraction from said chamber to a waste container.

8. The method of claim 7 comprising pumping said fraction by a peristaltic pump at a selected pump speed.

9. The method of claim 7 comprising adjusting the flow of said supernatant fraction exiting said separation chamber to said waste container through a pump-controlled waste line.

10. The method of claim 1 further comprising:
k) separating platelet rich plasma from said combined cellular fraction.

11. The method of claim 10 further comprising:
l) diverting said platelet rich plasma to a waste container.

12. The method of claim 1 further comprising:
k) combining said treated cell product and whole blood and concentrating mononuclear cells from the combined cellular fraction without further irradiation.

13. The method of claim 1 further comprising determining the amount of treated product to be introduced into said separation chamber.

* * * * *